US00RE46611E

(19) United States
(12) Reissued Patent
Zeidman

(10) Patent Number: US RE46,611 E
(45) Date of Reissued Patent: Nov. 21, 2017

(54) SWADDLING BLANKET AND POUCH COMBINATION

(71) Applicant: Hindi R. Zeidman, Upland, CA (US)

(72) Inventor: Hindi R. Zeidman, Upland, CA (US)

(21) Appl. No.: 15/056,928

(22) Filed: Feb. 29, 2016

Related U.S. Patent Documents

Reissue of:
(64) Patent No.: 7,774,875
Issued: Aug. 17, 2010
Appl. No.: 12/381,131
Filed: Mar. 6, 2009

U.S. Applications:
(63) Continuation of application No. 13/571,009, filed on Aug. 9, 2012, now Pat. No. Re. 45,903, which is an application for the reissue of Pat. No. 7,774,875.

(51) Int. Cl.
*A47G 9/08* (2006.01)
*A41B 13/06* (2006.01)

(52) U.S. Cl.
CPC ..... *A47G 9/083* (2013.01); *A41B 13/06* (2013.01)

(58) Field of Classification Search
CPC ..... A41B 13/06
See application file for complete search history.

(56) References Cited

U.S. PATENT DOCUMENTS 1,584,853 A * 5/1926 Dern ..... 2/69
2,812,516 A * 11/1957 Hoffman ..... A41B 13/04 2/227
2,989,753 A * 6/1961 Burner ..... 2/69.5
4,125,903 A 11/1978 Farrell
4,172,300 A * 10/1979 Miller ..... 5/424
4,979,250 A 12/1990 Troncone et al.
5,062,168 A * 11/1991 Kocib ..... 5/413 R
5,611,095 A 3/1997 Schneider
5,852,827 A * 12/1998 Lear ..... 2/69.5
6,145,932 A * 11/2000 Hamel-Nyhus et al. ..... 297/465
6,415,442 B1 7/2002 Smith
6,457,193 B1 10/2002 Li
6,868,566 B2 3/2005 Gatten
D504,753 S 5/2005 Gold et al.
6,928,674 B2 8/2005 Blackburn
7,043,783 B2 5/2006 Gatten
7,076,819 B2 7/2006 Trani et al.
7,150,055 B2 12/2006 Wootten, Jr.
7,181,789 B2 2/2007 Gatten
7,246,392 B2 7/2007 Schmid et al.
(Continued)

*Primary Examiner* — Matthew C Graham
(74) *Attorney, Agent, or Firm* — Knobbe Martens Olson & Bear LLP

(57) ABSTRACT

A swaddling blanket and pouch combination (SBPC) (10) that allows an infant to be comfortably and easily swaddled. The blanket (12) is comprised of a right blanket flap (28) and a left blanket flap (46) and includes a designated area to which is removably attached the pouch (70). The pouch features a lower end (78) which includes an opening and closing means that allows an infant's soiled diaper to be easily removed and replaced or to take a rectal temperature. The SBPC (10) is used by first placing the left blanket flap (46) over the pouch (70), which is then followed by placing the right blanket flap (28) over the pouch. The right and left blanket flaps (28,46) as well as the pouch (70) are preferably held in place by hook and loop fasteners (88).

11 Claims, 3 Drawing Sheets

(56) References Cited

U.S. PATENT DOCUMENTS

| | | | | |
|---|---|---|---|---|
| 7,254,849 | B1 * | 8/2007 | Fiebrich et al. | A41B 13/06 2/69.5 |
| 7,647,658 | B2 * | 1/2010 | Wilson | 5/482 |
| 7,774,875 | B1 | 8/2010 | Zeidman | |
| D691,781 | S | 10/2013 | Coates | |
| 8,793,813 | B2 | 8/2014 | Waters | |
| RE45,903 | E | 3/2016 | Zeidman | |
| 2008/0235848 | A1 * | 10/2008 | Wilder | A41B 13/06 2/69.5 |
| 2011/0231993 | A1 | 9/2011 | Schmid et al. | |
| 2012/0023637 | A1 | 2/2012 | Neveu | |
| 2014/0033431 | A1 | 2/2014 | Zeidman | |

* cited by examiner

SWADDLING BLANKET AND POUCH COMBINATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*PRIORITY INFORMATION*

*This application is a continuation reissue application of U.S. application Ser. No. 13/571,009, filed on Aug. 9, 2012, which is a reissue application of U.S. patent application Ser. No. 12/381,131, filed on Mar. 6, 2009, which issued on Aug. 17, 2010 as U.S. Pat. No. 7,774,875.*

*Notice: More than one reissue application has been filed for the reissue of U.S. Pat. No. 5,597,200. The reissue applications include this application and U.S. application Ser. No. 13/571,009, filed on Aug. 9, 2012, which will issue as U.S. Pat. No. Re. 45,903 on Mar. 1, 2016, which is a reissue application of U.S. Pat. No. 7,774,875.*

TECHNICAL FIELD

The invention generally pertains to the field of infant swaddling blankets, and more particularly to a swaddling blanket and pouch combination. The pouch, which is removably attached, is made of a resilient material and includes a lower end that can be opened to change an infant's diaper or to take a rectal temperature.

BACKGROUND ART

Archaeological records indicate that infant swaddling blankets were first used around 4000 B.C. in the desert regions of Central Asia in combination with a back-pack cradle board. As time progressed, the migration of people from region to region became a relatively permanent way of life. Swaddling subsequently also became a common part of child-rearing.

Early swaddling blankets consisted of a square piece of cloth. The infant was laid on the cloth diagonally and the corners of the cloth were folded over the feet, body and under the head, and the corners were tied to hold the blanket in position. A swaddling blanket typically formed the clothing for an infant until the infant was about a year old. The confinement provided by the swaddling blanket provided warmth and security for the infant who had recently left the mother's womb.

Today, swaddling is a standard newborn care practice in most hospitals and consists of swaddling blankets that are tucked and are useful for keeping the baby warm and comfortable, without increasing the risk of Sudden Infant Death Syndrome (SIDS), because the wrappings stay well clear of the baby's face and airway. By the time the infant learns to roll over, usually around 6 months, the infant should be sleeping in less restrictive coverings so it has more freedom to respond when the infant succeeds in rolling over.

Current infant swaddles are designed to make it easier to swaddle an infant than with traditional square sheets or blankets. Typical, swaddling blankets having flaps that fold around the infant's body or down and over the baby's shoulders and around and underneath the infant. These current swaddling blankets have the problem of having a wakeful infant loosening the blanket and kicking the swaddling blanket off. These problems are eliminated or at least minimized by the swaddling blanket and pouch combination disclosed in the instant patent application.

A search of the prior art did not disclose literature or patents that read directly on the claims of the instant invention, however the following U.S. patents are considered related:

| U.S. Pat. No. | INVENTOR | ISSUED |
|---|---|---|
| 7,181,789 | Gatten | 27 Feb. 2007 |
| 7,043,783 | Gatten | 16 May 2006 |
| 6,928,674 | Blackburn | 16 Aug. 2005 |
| 6,868,566 | Gatten | 22 Mar. 2005 |

The 7,181,789 patent discloses a swaddling blanket having a back panel that supports an infant from the neck to the feet, a leg pouch that loosely contains the infant's legs, arm restraints that hold the infant's arms against and parallel to the infant's torso, a tapered short blanket arm to wrap over the infant and a tapered long blanket arm. The long blanket arm is dimensioned to wrap around the infant more than once from the opposite direction to provide pressure around the infant's arms and torso.

The 7,043,783 patent discloses a swaddling blanket having a back panel that supports an infant from the neck to the feet, a leg pouch that loosely contains the infant's legs, arm restraints that hold the infant's arms against and parallel to the infant's torso, a tapered short blanket arm to wrap over the infant, and a tapered long blanket arm. The long blanket arm is dimensioned to wrap around the infant more than once from the opposite direction to provide pressure around the infant's arms and torso.

The 6,928,674 patent discloses a swaddling blanket which includes a tri-folded fabric sheet having a middle section with a pocket secured to an inner side of the fabric sheet on two adjacent sides to form a pouch. The pouch is dimensioned to receive an infant feet-first and is open on two other adjacent sides, and having left and right sections that border the middle section on opposite sides thereof and a width that is sufficient to overlap an infant in the middle section pocket. The left and right sections carry cooperating fasteners arranged to releasably secure the left and right sections to each other when overlapped abut an infant in the middle section pocket.

The 6,868,566 patent discloses a swaddling blanket having a back panel that supports an infant from the neck to the feet, a leg pouch that loosely contains the infant's legs, arm restraints that hold the infant's arms against and parallel to the infant's torso, a tapered short blanket arm to wrap over the infant, and a tapered long blanket arm. The long blanket arm is dimensioned to wrap around the infant more than once from the opposite direction to provide pressure around the infant's arms and torso.

For background purposes and as indicative of the art to which the invention relates, references may be made to the following remaining patents found in the search:

| U.S. Pat. No. | INVENTOR | ISSUED |
|---|---|---|
| 7,254,849 | Fiebrich et al | 14 Aug. 2007 |
| 7,076,819 | Trani et al | 18 Jul. 2006 |
| 6,457,193 | Li | 1 Oct. 2002 |
| 6,415,442 | Smith | 9 Jul. 2002 |
| 5,611,095 | Schneider | 18 Mar. 1997 |

-continued

| U.S. Pat. No. | INVENTOR | ISSUED |
|---|---|---|
| 4,979,250 | Troncone et al | 25 Dec. 1990 |
| 4,125,903 | Farrell | 21 Nov. 1978 |

DISCLOSURE OF THE INVENTION

The swaddling blanket and pouch combination (SBPC) improves current swaddling blankets by providing a swaddling blanket design that includes a pouch that is made of a resilient material that aids in maintaining a comfortable pressure on an infant placed into the pouch. The pouch includes a means for allowing a lower and a side section of the pouch to be opened to allow an infant's soiled diaper to be removed and changed or to take a rectal temperature.

In its basic design configuration the SBPC is comprised of:

A. A swaddling blanket having an inner surface and an outer surface, wherein the inner surface has a marked pouch attachment area having a first side and a second side. From the first side extends longitudinally a first blanket flap and from the second side extends longitudinally a second blanket flap. The first blanket flap has a longitudinal length that is greater than the longitudinal length of the second blanket flap, and B. A pouch having an inner surface with means for being removably attached to the marked pouch attachment area, an outer surface, an open upper end and a lower end. The lower end has means for being opened and closed to allow a diaper to be easily removed and replaced or to take a rectal temperature.

To utilize the SBPC, the second blanket flap is initially wrapped around the outer surface of the pouch and is attached thereto by an attachment means. After the second blanket flap is attached, the first blanket flap is wrapped around the second blanket flap and is attached thereto by the attachment means.

The means for attaching the inner surface of the pouch to the marked attachment area located on the swaddling blanket is selected from the group consisting of hook and loop fasteners, male and female detents and buttons. Likewise, the means for opening and closing the lower end of the pouch is selected from the group consisting of hook and loop fasteners, male and female detents and a zipper. The means for attaching the first and second blanket flaps is preferably a hook and loop fasteners.

In view of the above disclosure, the primary object of the invention is to provide a swaddling blanket and pouch combination that incorporates within a single article a swaddling blanket that has removably attached a pouch. The pouch features a lower end that is easily opened and closed to allow a diaper to be easily changed or to take a rectal temperature and can also include a removably attached infant head cover.

In addition to the primary object of the invention it is also an object of the invention to provide a swaddling blanket and pouch combination that:

- can be produced from various materials that will not gather at the infant's neck,
- can be produced in various dimensions to accommodate infants of various sizes,
- can be made of various colors such as a pink or a blue color to identify the sex of the infant,
- simulates a "womb-like" environment therefore is less traumatic on the infant,
- keeps the infant better positioned so the infant is less likely to turn, suffocate, and reduces the risk of SIDS,
- provides breath-ability so that the infant does not overheat,
- provides a pressure around the infant which is imperative for drug-exposed infants, and
- is cost effective from both a consumer's and manufacturer's point of view.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms of a preferred embodiment for a swaddling blanket and pouch combination (SBPC) that is designed to improve current designs of swaddling blankets by including an infant pouch which is made of a resilient material that maintains a comforting pressure on an infant that is placed into the pouch. The pouch is removably attached and includes closeable lower and side openings that allow a diaper to be easily removed and a clean diaper attached or to take a rectal temperature.

The preferred embodiment of the SBPC 10, as shown in FIGS. 1-7, is comprised of the two major elements: a swaddling blanket 12 and a pouch 70.

Figure 2:
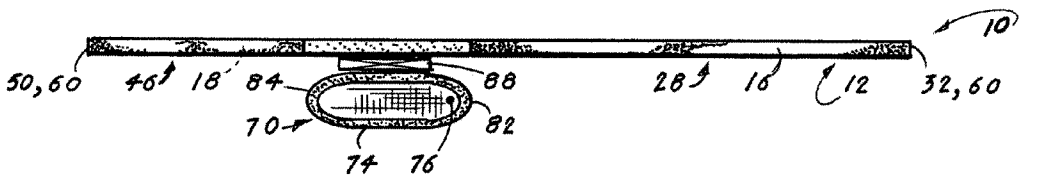
FIG. 2 is a top plan view of the SBPC.
Figure 1:
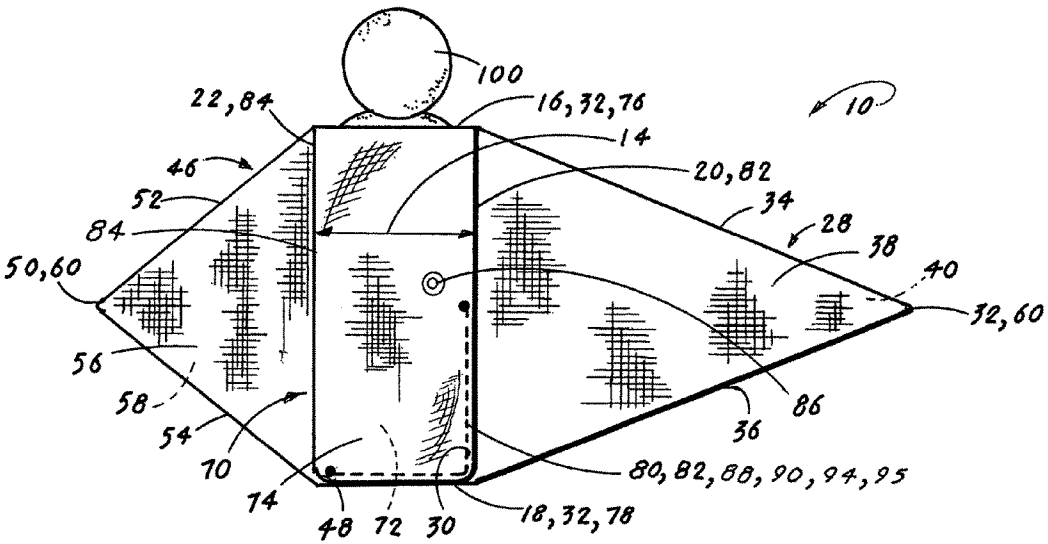
FIG. 1 is a front elevational view of the swaddling blanket and pouch combination (SBPC) showing the pouch attached between a right blanket flap and a left blanket flap, and with an infant inserted into the pouch.
Figure 3:
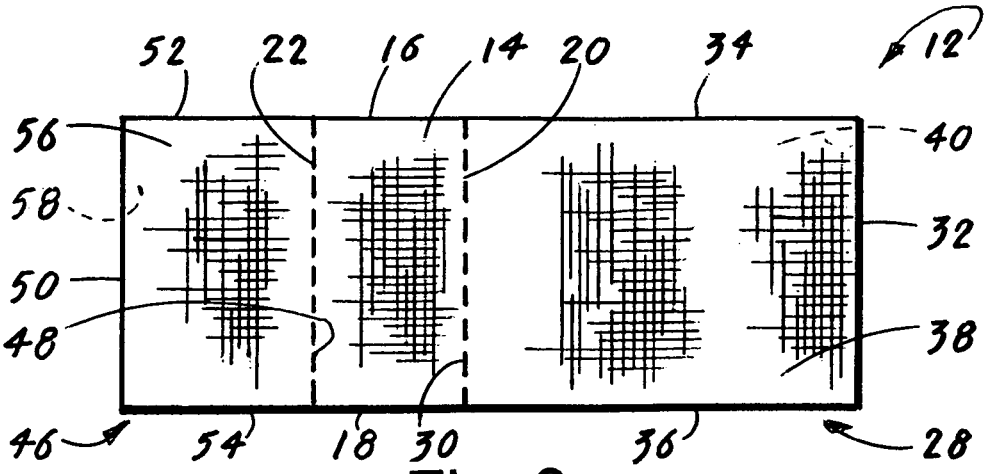
FIG. 3 is an elevational view of a swaddling blanket having the upper and lower edges of the right and left blanket flaps in alignment with the respective upper and lower edges of the blanket.
Figure 4:
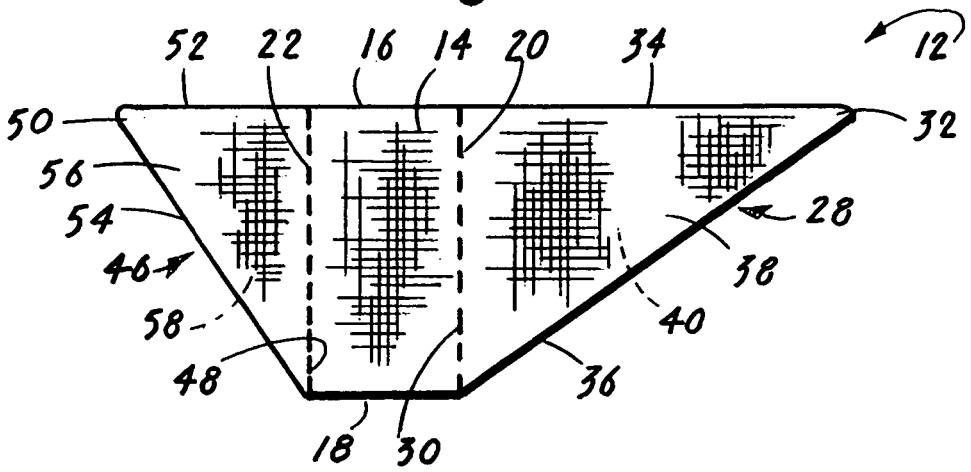
FIG. 4 is an elevational view of a swaddling blanket that has the upper edges of the right and left blanket flaps in alignment with the respective upper edge of the blanket, and the lower edges of the right and left blanket flaps angled upward.
Figure 5:
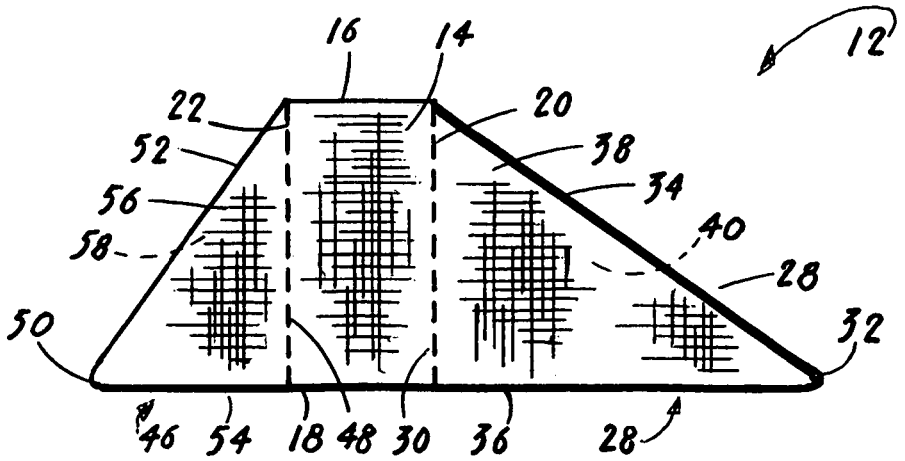
FIG. 5 is an elevational view of a swaddling blanket having the upper edge of the right and left blanket flaps angled downward, and with the lower edges of the right and left blanket flaps in alignment with the respective lower edges of the blanket.

The swaddling blanket 12, as shown attached to the pouch 70 in FIGS. 1 and 2, and detached from the pouch 70 in FIGS. 3, 4 and 5, includes a pouch attachment area 14, as shown best in FIGS. 3-5, and is comprised of an upper edge 16, a lower edge 18, a right pouch border attachment mark 20 and a left pouch border attachment mark 22. The two border attachment marks 20,22 are shown in broken lines, in FIGS. 3-5, and function to outline the area 14 in which area the pouch 70 is removably attached. The swaddling blanket 12 also includes a right blanket flap 28 and a left blanket flap 46.

The right blanket flap 28 is further comprised of a inner edge 30 that is integral with the right pouch border attachment mark 20, an outer edge 32, an upper edge 34, a lower edge 36, an inner surface 38 and an outer surface 40. Likewise, the left blanket flap 46, as also shown in FIGS. 1-5, is further comprised of an inner edge 48 that is integral with the left pouch border attachment mark 22, an outer edge 50, an upper edge 52, a lower edge 54, an inner surface 56 and an outer surface 58.

As shown in FIGS. 1-5, the longitudinal length of the left blanket flap 46, as measured from the left pouch border attachment mark 22, is less than the longitudinal length of the right blanket flap 28. With this arrangement, the left blanket flap 46 is folded Over the pouch 20 prior to folding the right blanket flap 28, as described infra and shown in FIG. 7. The swaddling blanket is made of a material that is selected from the group consisting of wool, cotton and waterproof nylon.

The blanket's 12 right blanket flap 28 and left blanket flap 46 can be configured in at least four different shapes. In the first shape, as shown in FIG. 1, the upper edges 34,52 of the right and left blanket flaps 28,46 are angled downward from the respective upper edge 16 of the blanket 12. The lower edges 36,54 of the right and left blanket flaps 28,46 are angled upward from the respective lower edge 18 of the blanket 12. The right and left blanket flaps 28,46 terminate at an outer edge 32,50 configured as a centered radiused apex 60.

The second shape, as shown in FIG. 3, the upper edges 34,52 of the right and left blanket flaps 28,46 are in respective alignment with the upper edge 16 of the blanket, and the lower edges 36,54 of the right and left blanket flaps 28,46 are in respective alignment with the lower edge 18 of the blanket.

Third shape, as shown in FIG. 4, the upper edges 34,52 of the right and left blanket flaps 28,46 are in alignment with the respective upper edge 16 of the blanket 12. The lower edges 36,54 of the right and left blanket flaps 28,46 are angled upward from the respective lower edge 18 of the blanket 12. The right and left blanket flaps 28,46 terminate at an outer edge 32,58 configured as an off-centered radiused apex 62.

The fourth shape, as shown in FIG. 5, the upper edges 34,52 of the right and left blanket flaps 28,46 are angled downward from the respective upper edge 16 of the blanket. The lower edges 36,54 of the right and left blanket flaps 28,46 are in alignment with the respective lower edge 18 of the blanket 12. The right and left blanket flaps 28,46 terminate at an outer edge 32,50 configured as an off-centered radiused apex 62.

Figure 7:
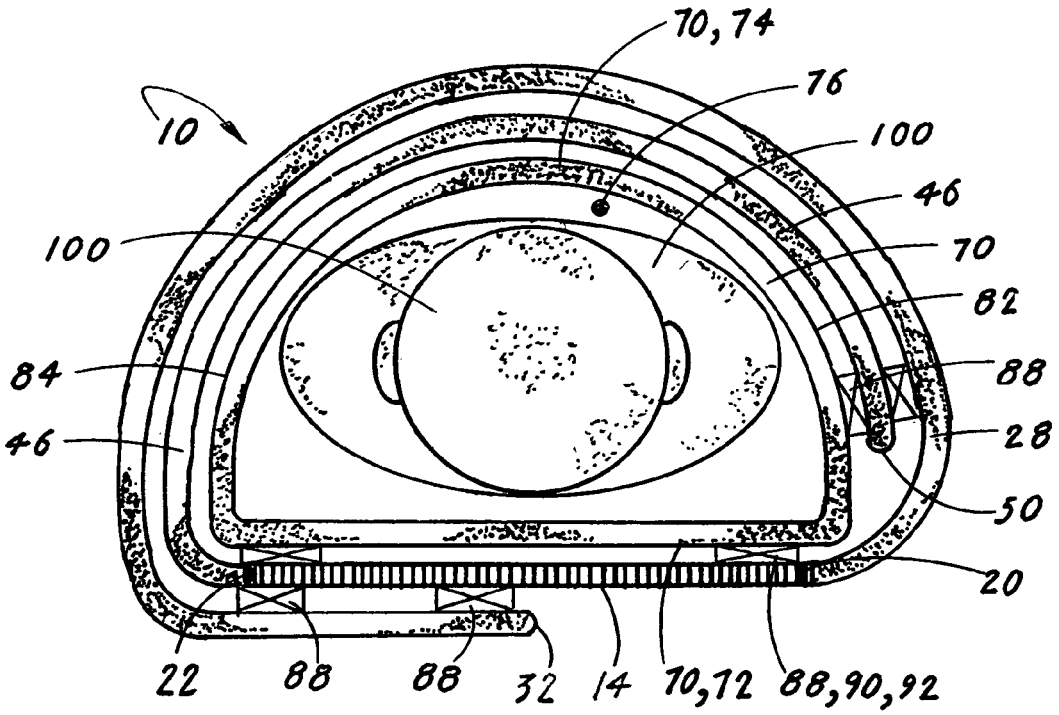
FIG. 7 is a top plan view of the SBPC showing the right and left blanket flaps wrapped around the pouch.
Figure 6:
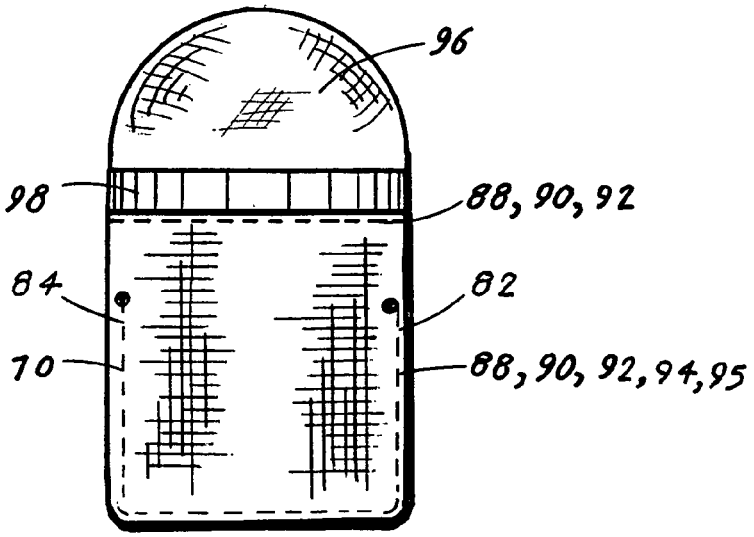
FIG. 6 is a front elevational view of a pouch that includes a removably attached infant head cover.

The pouch 70, which is the second major element of the SBPC 10, is shown attached to the swaddling blanket 12 in FIGS. 1, 2 and 7, and detached from the swaddling blanket 12 in FIG. 6. The pouch 70 is comprised of an inner section 72, an integrally attached outer section 74, an open upper end 76, a lower end 78, a side end 80 and a left side 84. The pouch is made of a resilient soft material that maintains a comfortable pressure on the infant 100 placed into the pouch 70, as shown in FIG. 7. The resilient soft material is selected from the group consisting of cotton spandex. stretch denim, stretch vinyl and stretch velvet.

The inner section 72 is dimensioned to be attached by an attachment means 86 to the area bordered by the right and left pouch border attachment marks 20,22 which are located on the swaddling blanket 12, as shown best in FIGS. 3-5. The lower edges 36,54 of the blanket 12 are located in substantial alignment with the lower end 18, as shown in FIG. 1. Alternatively, the lower edges 36,54 can extend above the lower end 78 of the pouch 70 (not shown). As shown best in FIG. 7, the inner section 72 of the pouch 70 can be attached to the pouch attachment area 14 by hook and loop fasteners 88, male and female detents 90, and buttons 92.

The pouch 70, as shown in FIG. 1, includes a closeable lower end 78 that interfaces with a closeable side end 80 and continues partially along either the pouch's right side 82, or the pouch's left side 84 (not shown) or along both the right side 82 and the left side 84. The closeable lower end 78 and the side ends 80 and 84 allow the pouch 70 to be easily opened to allow a diaper to be easily removed and replaced or to take a rectal temperature. The lower and side openings are closed by an attachment means that is selected from the group consisting of hook and loop fasteners 88, male and female detents 90, a zipper 94 and a drawstring 95.

As shown in FIG. 6, the pouch 70 can also be designed to include an infant head cover 96 that applies a comforting pressure around the infant's head, The cover 96 can be designed to extend from the open upper end 76 located on the pouch 70 or from the upper edge 16 of the blanket 12. The cover is removably attached by an attachment means that is selected from the group consisting of hook and loop fasteners 88, male and female detents 90 and buttons 92. The infant head cover 96 is made of a resilient soft material that is selected from the group consisting of spandex stretch denim, stretch vinyl or stretch velvet. The head cover 96 can also be made to include a low-resistance elastic band 98 that provides additional security to the cover 96. In FIG. 6, is also shown a closeable lower end 78 and sides 82 and 84 that are closeable by either hook and loop fasteners 88, male/female detents 90, buttons 92, a zipper 94 and a drawstring 95. FIG. 6, is also shown a closeable lower end 78 and sides 82 and 84 that are closeable by either hook and loop fasteners 88, male/female detents 90, buttons 92, a zipper 94 and a drawstring 95.

To utilize the SBPC 10, as shown in FIG. 7, the left blanket flap 46 commencing from the left pouch border attachment mark 22 is wrapped sequentially around the pouch's left side 84, the outer section 74 and with the outer edge 50 of the left blanket flap 46 attached by hook and loop fasteners 88 to the right side 82 of the pouch 70. Likewise, the right blanket flap 28 commencing from the right pouch border attachment mark 20 is wrapped sequentially around the left blanket flap 46 that is attached to the right side 82 of the pouch 70, around the outer and left side section 74,84 of the pouch 70 with the outer edge 32 of the right blanket flap 28 attached by hook and loop fasteners 88, to the left blanket flap 46 that is attached to the inner section 72 of the pouch 70. As shown in FIG. 1, the pouch is dimensioned to allow an infant to be placed into the pouch 70, with the infant's arms located internally within the pouch 70 or with the infant's arms located externally to the pouch 70. As also shown in FIG. 1, the pouch 70 has a length that preferably places the open upper end 76 of the pouch adjacent to the chest area of an infant. The lower end 78 of the pouch 70 is preferably located adjacent to the lower edge 18 of the swaddling blanket 12.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and the scope of the claims.

Swaddling Blanket and Pouch Combination

Element Designation

| | |
|---|---|
| 10 | Swaddling Blanket and Pouch Combination |
| 12 | Swaddling Blanket |
| 14 | Pouch Attachment Area |
| 16 | Upper Edge |
| 18 | Lower Edge |
| 20 | Right Pouch Border Attachment Mark |
| 22 | Left Pouch Border Attachment Mark |
| 24 | |
| 26 | |
| 28 | Right Blanket Flap |
| 30 | Inner Edge |
| 32 | Outer Edge |
| 34 | Upper Edge |
| 36 | Lower Edge |
| 38 | Inner Surface |
| 40 | Outer Surface |
| 42 | |
| 44 | |
| 46 | Left Blanket Flap |
| 48 | Inner Edge |
| 50 | Outer Edge |
| 52 | Upper Edge |
| 54 | Lower Edge |
| 56 | Inner Surface |
| 58 | Outer Surface |
| 60 | Centered Radiused Apex |
| 62 | Off-Centered Radiused Apex |
| 64 | |
| 66 | |
| 68 | |
| 70 | Pouch |
| 72 | Inner Section |
| 74 | Outer Section |
| 76 | Open Upper End |
| 78 | Closeable Lower End |
| 80 | Closeable Side End |
| 82 | Right Side |
| 84 | Left Side |
| 86 | Attachment Means |
| 88 | Hook and Loop Fasteners |
| 90 | Male/Female Detents |
| 92 | Buttons |
| 94 | Zipper |
| 95 | Drawstring |
| 96 | Infant Head Cover |
| 98 | Elastic Band |
| 100 | Infant |

The invention claimed is:

[1. A swaddling blanket and pouch combination (SBPC) comprising:

a) said swaddling blanket having an inner surface and an outer surface, wherein the inner surface has a marked pouch attachment area form where laterally extends a right blanket flap and a left blanket flap, wherein the left blanket flap has a longitudinal length that is less than the longitudinal length of the right blanket flap, and b) said pouch having an inner surface with means for being removably attached to the marked pouch attachment area, an outer surface, an open upper end and a lower end having means for being opened and closed to allow a diaper to be easily removed and replaced or to take a rectal temperature, wherein said means for removably attaching the inner surface of said pouch to the marked pouch attachment area located on said swaddling blanket is selected from the group consisting of hook and loop fasteners, male and female detents and buttons, wherein to utilize said SBPC the left blanket flap is initially wrapped around the outer surface of said pouch, which is then followed by wrapping the right blanket flap over and around the left blanket flap.]

[2. A swaddling blanket and pouch combination (SBPC) comprising:

a) said swaddling blanket having an inner surface and an outer surface, wherein the inner surface has a marked pouch attachment area from where laterally extends a right blanket flap and a left blanket flap, wherein the left blanket flap has a longitudinal length that is less than the longitudinal length of the right blanket flap, and b) said pouch having an inner surface with means for being removably attached to the marked pouch attachment area, an outer surface, an open upper end and a lower end having means for being opened and closed to allow a diaper to be easily removed and replaced or to take a rectal temperature, an infant head cover that is removably attached to the open upper end of said pouch by means of hook and loop fasteners, male and female detents and buttons, wherein to utilize said SBPC the left blanket flap is initially wrapped around the outer surface of said pouch, which is then followed by wrapping the right blanket flap over and around the left blanket flap.]

3. A [swaddling blanket and pouch combination (SBPC)] *swaddle* comprising:

[A. said swaddling blanket comprising:

a) a pouch attachment] *an* area [having:] *comprising*

[(1) an upper edge, (2) a lower edge, (3) a right pouch border attachment mark] *a first area side*, and

[(4) a left pouch border attachment mark,] *a second area side;*

[b) a right blanket] *a first* flap [having:] *comprising*

[(1) an] *a first* inner [edge that is integral with the right pouch border attachment mark] *portion proximal the first area side, and*

[(2) an] *a first* outer [edge,] *portion;*

[(3) an upper edge, (4) a lower edge, (5) an inner surface and (6) an outer surface, c) a left blanket] *a second* flap [having:] *comprising*

[(1) an] *a second* inner [edge that is integral with the left pouch border attachment mark] *portion proximal the second area side, and*

[(2) an] *a second* outer [edge,] *portion; and*

[(3) an upper edge, (4) a lower edge, (5) an inner surface and (6) an outer surface, wherein the longitudinal length of said left blanket flap is less than the longitudinal length of said right blanket flap, B. said] *a* pouch [having:], *sized and configured to allow an infant to be placed partially into the pouch, the pouch comprising*

[a) an inner section that is dimensioned to be attached by an attachment means to the area bordered by the right and left pouch border attachment marks located on said swaddling blanket, b) an integrally attached outer section] *an outward-facing portion,*

[c)] an open [upper and] *portion*,

[d)] a [closeable] lower end [and side end],

[e) a right] *a first pouch* side, [and g) a left] *a second pouch* side, *and*

*a recloseable portion spaced apart from the open portion and extending along a segment of the lower end and along 1) a first segment of the first pouch side, or 2) a second segment of the second pouch side, or 3) the first segment of the first pouch side and the second segment of the second pouch side,* wherein [to utilize said SBPC], *in use,* the [left blanket] *second* flap [commencing from the left pouch border attachment mark] is wrapped [sequentially] around [said pouch's inner section, the left side, the outer section and with the outer edge of the left blanket flap attached by an attachment means to the right side of said pouch, likewise] *the second pouch side and the outward-facing portion of the pouch*, the [right blanket] *first* flap is wrapped [sequentially] around [the left blanket flap that is attached to the right side of said pouch, around the outer and left side section of said pouch with] *the first pouch side and the outward-facing portion of the pouch, and* the *first* outer [edge] *portion* of the [right blanket] *first* flap *is configured to be* attached by [the attachment means] *one or more fasteners* to the [left blanket] *second* flap [that is attached to the inner section of said pouch, wherein said pouch is dimensioned to allow an infant to be placed into said pouch, with the infant's arms located internally within said pouch or with the infant's arms located externally to said pouch].

4. The [swaddling blanket and pouch combination] *swaddle* as specified in claim 3 wherein *the first flap comprises a first lower portion, the second flap comprises a second lower portion, and* said pouch [has a length that preferably places] *is sized and configured such that, when in use,* the open [upper end] *portion* of said pouch [adjacent to] *is near* the chest area of [an] *the* infant and the [lower end] *recloseable portion* of said pouch [adjacent to] *is near* the *first* lower [edge of said swaddling blanket] *portion of the first flap and the second lower portion of the second flap*.

5. The [swaddling blanket and pouch combination] *swaddle* as specified in claim [4] *3* wherein said pouch is made of a resilient, soft material [that applies] *configured to apply* a comforting pressure around the infant.

6. The [swaddling blanket and pouch combination] *swaddle* as specified in claim 5 wherein the resilient, soft material [is] *comprises one or more fabrics* selected from the group consisting of cotton, spandex, stretch denim, stretch vinyl and stretch velvet.

7. The [swaddling blanket and pouch combination] *swaddle* as specified in claim 3 wherein said [means for attaching the inner section of said pouch to the pouch attachment area on said swaddling blanket is selected from the group consisting of] *one or more fasteners comprises* hook and loop fasteners[, male and female detents, and buttons].

[8. The swaddling blanket and pouch combination as specified in claim 3 wherein the closeable lower end of said pouch further comprises an opening and closing means that extends along the lower end of said pouch and continuous partially along either the right or the left side of said pouch, wherein the opening and closing means allows said pouch to be opened to allow a soiled diaper to be easily removed and replaced or to take a rectal temperature.]

9. The [swaddling blanket and pouch combination] *swaddle* as specified in claim [8] *3, further comprising means for opening and closing the recloseable portion,* wherein the *opening and closing* means [for opening and closing said pouch means is selected from the group consisting of] *comprises* hook and loop fasteners, male and female detents, a zipper [and], *or* a drawstring.

[10. The swaddling blanket and pouch combination as specified in claim 3 wherein said pouch further comprises an infant head cover that is removably attached to and extends from the open upper end of said pouch.]

[11. The swaddling blanket and pouch combination as specified in claim 10 wherein said infant head cover is removably attached to the upper end of said pouch or to the upper edge of said blanket by an attachment means that is selected from the group consisting of hook and loop fasteners, male and female detents and buttons.]

[12. The swaddling blanket and pouch combination as specified in claim 10 wherein said infant head cover is made of a resilient, soft material that is selected from the group consisting of cotton, spandex, stretch denim, stretch vinyl and stretch velvet.]

13. The [swaddling blanket and pouch combination] *swaddle* as specified in claim 3 wherein:

[a) ] the *first flap further comprises a first* upper [edges of the right and left blanket flaps are angled downward from the respective upper edge of said blanket, and] *edge angled downward from the first inner portion to the first outer portion and a first lower edge angled upward from the first inner portion to the first outer portion, and*

*the second flap further comprises a second upper edge angled downward from the second inner portion to the second outer portion and a second lower edge angled upward from the second inner portion to the second outer portion,*

[b) the lower edges of the right and left blanket flaps are angled upward from the respective lower edge of said blanket,] wherein the [right] *first flap terminates at a first centered radiused apex* and [left blanket flaps terminate] *the second flap terminates* at [an outer edge configured as] a *second* centered radiused apex.

14. The [swaddling blanket and pouch combination] *swaddle* as specified in claim 3 wherein*:*

*the first flap further comprises a first upper edge and a first lower edge,*

*the second flap further comprises a second upper edge and a second lower edge,* the *first* upper [edges of the right and left blanket flaps are in respective alignment with the upper edge of said blanket] *edge of the first flap and the second upper edge of the second flap are generally aligned and generally parallel*, and the *first* lower [edges of the right and left blanket flaps are in respective alignment with the lower edge of said blanket] *edge of the first flap and the second lower edge of the second flap are generally aligned and generally parallel*.

15. The [swaddling blanket and pouch combination] *swaddle* as specified in claim 3 wherein:

*the first flap further comprises a first upper edge and a first lower edge,*

*the second flap further comprises a second upper edge and a second lower edge,*

[a)] the *first* upper [edges of said right and left blanket flaps are in alignment with the respective upper edge of said blanket] *edge of the first flap and the second upper edge of the second flap are generally aligned and generally parallel*, [and b)] the *first* lower [edges of said right and left blanket flaps are angled upward from the respective lower edge of said blanket, wherein] *edge of the first flap is angled upward from the first inner portion to the first outer portion, and the second lower edge of the second flap is angled upward from the second inner portion to the second outer portion, and* the [right] *first flap terminates at a first off-centered radiused apex* and [left blanket flaps terminate in an outer edge configured as an] *the second flap terminates at a second* off-centered radiused apex.

16. The [swaddling blanket and pouch combination] *swaddle* as specified in claim 3 wherein:

*the first flap further comprises a first upper edge and a first lower edge,*

*the second flap further comprises a second upper edge and a second lower edge,*

[a)] the *first* upper [edges of said right and left blanket flaps are angled downward from the respective upper edge of said blanket, and] *edge of the first flap is angled downward from the first inner portion to the first outer portion and the second upper edge of the second flap is angled downward from the second inner portion to the second outer portion,*

[b)] the *first* lower [edges of said right and left blanket flaps are in alignment with the respective lower edge of said blanket, wherein] *edge of the first flap and the second lower edge of the second flap are generally aligned and generally parallel, and* the [right] *first flap terminates at a first off-centered radiused apex* and [left blanket flaps terminate at an outer edge configured as an ] *the second flap terminates at a second* off-centered radiused apex.

[17. The swaddling blanket and pouch combination as specified in claim 3 wherein said swaddling blanket is made of a material that is selected from the group consisting of wool, cotton, and waterproof nylon.]

*18. The swaddle as specified in claim 3, the pouch configured to be removably attached to the area.*

* * * * *